US007306791B2

(12) United States Patent
Arisawa et al.

(10) Patent No.: US 7,306,791 B2
(45) Date of Patent: Dec. 11, 2007

(54) AGENT FOR PREVENTING AND/OR TREATING MULTIPLE ORGAN FAILURE

(75) Inventors: Hirohiko Arisawa, Minamikawachi-machi (JP); Hiroaki Masunaga, Mibu-machi (JP); Hiromi Ogawa, Utsunomiya (JP); Kanji Higashio, Kawagoe (JP)

(73) Assignee: Daiichi Sankyo Co., Ltd., Tokyo (JP)

( * ) Notice: Subject to any disclaimer, the term of this patent is extended or adjusted under 35 U.S.C. 154(b) by 177 days.

(21) Appl. No.: 10/317,011

(22) Filed: Dec. 11, 2002

(65) Prior Publication Data
US 2003/0153489 A1 Aug. 14, 2003

Related U.S. Application Data

(63) Continuation of application No. 09/180,599, filed as application No. PCT/JP98/00998 on Mar. 11, 1998, now abandoned.

(30) Foreign Application Priority Data

Mar. 11, 1997 (JP) ................... 9-074372
May 30, 1997 (JP) ................... 9-157645

(51) Int. Cl.
A61K 45/00 (2006.01)
A61K 38/16 (2006.01)
C07K 17/00 (2006.01)

(52) U.S. Cl. ................... 424/85.1; 514/8; 514/21; 514/970; 530/395; 530/399

(58) Field of Classification Search ............... 424/85.1; 514/8, 21, 970; 530/395, 399
See application file for complete search history.

(56) References Cited

U.S. PATENT DOCUMENTS

| 3,904,753 | A | 9/1975 | Sonenberg et al. |
| 4,076,701 | A | 2/1978 | Burton et al. |
| 4,481,137 | A | 11/1984 | Ohnishi et al. |
| 4,490,549 | A | 12/1984 | Johnson |
| 4,650,674 | A | 3/1987 | Aggarwal et al. |
| 4,767,701 | A | 8/1988 | Burton et al. |
| 4,777,241 | A | 10/1988 | Irikura et al. |
| 4,822,605 | A | 4/1989 | Powell |
| 4,870,163 | A | 9/1989 | Rubin et al. |
| 5,091,511 | A | 2/1992 | Sone et al. |
| 5,328,836 | A | 7/1994 | Shima et al. |
| 5,362,716 | A | 11/1994 | Kmiecik et al. |
| 5,432,267 | A | 7/1995 | Kusama et al. |
| 5,510,327 | A | 4/1996 | Hayasaka et al. |
| 5,547,856 | A | 8/1996 | Godowski et al. |
| 5,587,359 | A | 12/1996 | Higashio et al. |
| 5,589,451 | A | 12/1996 | Wilson |
| 5,606,029 | A | 2/1997 | Degen |
| 5,648,233 | A | 7/1997 | Yamaguchi et al. |
| 5,648,273 | A | 7/1997 | Bottaro et al. |
| 5,658,742 | A | 8/1997 | Higashio et al. |
| 5,703,047 | A | 12/1997 | Wilson |
| 5,703,048 | A | 12/1997 | Roos et al. |
| 5,707,624 | A | 1/1998 | Nickoloff et al. |
| 5,714,461 | A | 2/1998 | Masunaga et al. |
| 5,760,177 | A | 6/1998 | Iwanaga et al. |
| 5,776,464 | A | 7/1998 | Nakamura |
| 5,821,223 | A | 10/1998 | Rubin et al. |
| 5,998,370 | A | 12/1999 | Arai |
| 6,306,827 | B1 | 10/2001 | Kinosaki et al. |
| 6,333,309 | B1 | 12/2001 | Higashio |
| 2002/0041863 | A1 | 4/2002 | Kojiro et al. |
| 2003/0082134 | A1 | 5/2003 | Kojiro et al. |
| 2003/0236191 | A1 | 12/2003 | Kijiro et al. |

FOREIGN PATENT DOCUMENTS

| CA | 2218864 A1 | 10/1996 |
| CA | 2100720 C | 3/2003 |
| CA | 2116192 C | 5/2005 |
| EP | 0 322 084 A2 | 6/1989 |
| EP | 0 456 188 A1 | 11/1991 |
| EP | 0 462 549 A1 | 12/1991 |
| EP | 0 498 680 A1 | 8/1992 |
| EP | 0 519 728 A2 | 12/1992 |
| EP | 0 587 311 A1 | 3/1994 |

(Continued)

OTHER PUBLICATIONS

Cross et al., Infection and Immunity, vol. 61, pp. 2741-2747, 1993.*
Fink et al., Journal of Surgical Research, vol. 49, pp. 186-196, 1990.*
Roger C. Bone, Annals of Internal Medicine, vol. 115, No. 6, pp. 457-469, 1991.*
Glauser et al., The Lancet, vol. 338, pp. 732-736, 1991.*
Richman et al. Peritubular Capillaries A Major Target Site of Endotoxin-Induced Injury in the Primate Kidney. 1980, Laboratory Investigation, vol. 43, No. 4, pp. 327-332.*

(Continued)

Primary Examiner—Jon Weber
Assistant Examiner—Abdel A. Mohamed
(74) Attorney, Agent, or Firm—Kirkpatrick & Lockhart Preston Gates Ellis LLP

(57) ABSTRACT

The present invention provides methods of preventing and/or treating multiple organ failure comprising the step of administering a therapeutically effective amount of agent comprising tumor cytotoxic factor-II (TCF-II) or hepatocyte growth factor (HGF). Methods of the present invention will be useful for preventing and/or treating the development of multiple organ failure resulting from burn, disseminated intravascular coagulation (DIC), circulatory failure, hemorrhagic shock, infectious disease, acute pancreatitis, ischemic disorder, hepatorenal syndrome, gastrointestinal hemorrhage, nutritional metabolic failure, terminal cancer, acquired immunodeficiency syndrome (AIDS), deterioration of systemic conditions due to radiation affection, and cachexia.

4 Claims, 5 Drawing Sheets

FOREIGN PATENT DOCUMENTS

| | | |
|---|---|---|
| EP | 0 588 477 A2 | 3/1994 |
| EP | 0588477 A2 * | 3/1994 |
| EP | 0 604 184 A1 | 6/1994 |
| EP | 0 604 185 A1 | 6/1994 |
| EP | 0 462 277 B1 | 6/1995 |
| EP | 0 724 884 A1 | 8/1996 |
| EP | 0 757 994 A1 | 2/1997 |
| EP | 0 821 969 A2 | 2/1998 |
| EP | 0 461 560 B1 | 11/1998 |
| EP | 0 539 590 B1 | 3/1999 |
| EP | 0 914 829 A1 | 5/1999 |
| EP | 0 925 791 A1 | 6/1999 |
| EP | 0 950 416 A1 | 10/1999 |
| EP | 0 982 037 A1 | 3/2000 |
| EP | 0 612 530 B1 | 11/2000 |
| EP | 0 653 211 B1 | 10/2001 |
| EP | 0 672 685 B1 | 8/2002 |
| EP | 0 891 778 B1 | 6/2004 |
| JP | 6-56692 | 3/1989 |
| JP | 10-68400 | 3/1989 |
| JP | 5244976 | 9/1993 |
| JP | 6-40935 | 2/1994 |
| JP | 6-40938 | 2/1994 |
| JP | 6040934 | 2/1994 |
| JP | 6116299 | 4/1994 |
| JP | 8176007 | 7/1996 |
| JP | 6340546 | 8/1996 |
| JP | 8231418 | 9/1996 |
| JP | 10029951 | 2/1998 |
| JP | 10194986 | 7/1998 |
| JP | 10273446 | 10/1998 |
| WO | WO90/10651 | 9/1990 |
| WO | WO91/03254 | 3/1991 |
| WO | WO93/08821 | 5/1993 |
| WO | WO93/13066 | 7/1993 |
| WO | WO94/14845 | 7/1994 |
| WO | WO96/20004 | 7/1996 |
| WO | WO96/20214 | 7/1996 |
| WO | WO96/28423 | 9/1996 |
| WO | WO96/32960 | 10/1996 |
| WO | WO98/40096 | 9/1998 |
| WO | WO98/41230 | 9/1998 |
| WO | WO98/43665 | 10/1998 |
| WO | WO99/47155 | 9/1999 |

OTHER PUBLICATIONS

Igawa et al. Hepatocyte growth factor may function as a renotropic factor for regeneration in rats with acute renal injury. 1993, Am. J. Physiol., vol. 265, pp. 61-69.*

American College of Surgeons Committee on Trauma, (1982), "Early Care of the Injured Patient," 3rd ed, Philadelphia, pp. 24-27.

Anscher et al., (1994), "Role of Transforming Growth Factor-β And Hepatocyte Growth Factor in Late Normal Tissue Effects of Radiation," *Radiat. Oncol. Invest.*1(6):305-13.

Argiles et al, (1999), "The Role of Cytokines in Cancer Cachexia," *Med. Res. Rev.*, 19 (3):223-48.

Ashorn, et al., (1990), "An Inhibitor of the Protease Blocks Maturation of Human and Simian Immunodeficiency Viruses and Spread of Infection," *Proc. Natl. Acad. Sci.*, 87:7472-7476.

Baldwin, et al., (1995), "Structure of HIV-1 Protease with KNI-272, A Tight-Binding Transition-State Analog Containing of Allophenylnorstatine," *Structure*, 3(6):81-588.

Bertevello et al., (2001), "Heterogeneous Response of Adipose Tissue to Cancer Cachexia," *Braz. J. Med. Biol. Res.*, 34(9:1161-1167.

Bossola et al., (2000) "Serum Tumour Necrosis Factor-α Levels in Cancer Patients are Discontinuous and Correlate with Weight Loss," *European Journal of Clinical Investigation*, 30:1107-1112.

Cainzos, et al., (1997), "Septic Complications after Billiary Tract Stone Surgery: A Review and Report of the European Prospective Study," *Hepato-Gastroenterology*, 44:959-967.

Ceconi, et al., (1998), "Tumor Necrosis Factor in Congestive Heart Failure: A Mechanism of Disease for the New Millennium," *Progress in Cardiovascular Diseases*, 41(1)(Suppl. 1):25-30.

Cerra et al., (1987), "Hypermetabolism, organ failure, and metabolic support," *Surgery*, vol. 101, 1-14.

Chang, et al., (1998), "The Role of Cytokines in the Catabolic Consequences of Infection and Injury," *Journal of Parenteral and Enteral Nutrition*, 22(3):156-166.

Debouck, et al., (1990), "Human Immunodeficiency Virus Protease; A Target for AIDS Therapy," Drug Development Research, 21:1-17.

Deitch, (1992), "Multiple Organ Failure," *Annals of Surgery*, 216(2):117-134.

Deitch et al., (1999), "Prevention of Multiple Organ Failure," *Surgical Clinics of North America*, 79(6):1471-1488.

Dube et al., (1988), "Glycosylation at Specific Sites of Erythropoietin Is Essential for Biosyntheis, Secretion, and Biological Function," *Journal of Biological Chemistry*, 263(33):17516-17521.

Fahey et al., (1992), "Status of Immune-Based Therapies In HIV Infection and AIDS" *Clin., Exp. Immunol.*, 88:1-5.

Fox, (1994), "No Winners Against AIDS," *Bio/Technology*,, 12:128.

Fujiwara et al., (1993), "Stimulation of Liver Growth by Exogenous Human Hepatocyte Growth Factor in Normal and Partially Hepatectomized Rats," *Hepatology*, 18(6):1443-1449.

Gohda et al., (1988), "Purification and Partial Characterization of Hepatocyte Growth Factor from Plasma of a Patient with Fulminant Hepatic Failure," *The American Society for Clinical Investigation*, 81:414-419.

Goodman & Gilman, *The Pharmacological Basis of Therapeutics*, 9th Edition, pp. 1654-1659.

Goto, M. et al., "Production of Recombinant Human Erythropoietin in mammalian Cells: Host-Cell Dependency of the Biological Activity of the Cloned Glycoprotein." *Bio/Technology*, vol. 6, pp. 67-71 (Jan. 1988).

Gross et al., (1993), "Inflammatory Mediators and Cytokines - New Aspects of the Pathophysiology and Assessment of Severity of Acute Pancreatitis?," *Hepato-Gastroenterol.*, 40:522-530.

Gulnik, et al., (1995), "Kinetic Characterization and Cross-Resistance Patterns of HIV-1 Protease Mutants A Selected under Drug Pressure," *Biochemistry*, 34:9282-9287.

Harris, (1997), "Growth Factors and Cytokines in Acute Renal Failure," *Advances in Renal Replacement Therapy*, 4(2)(Suppl. 1):43-53.

Haslett, (1998), "Anticytokine Approaches to the Treatment of Anorexia and Cachexia, Seminars in Oncology," *Seminars in Oncology*, 25(2)(Suppl. 6):53-57.

Haynes et al., (1996), "Update on the Issues of HIV Vaccine Development," *Annals of Medicine*, 28:39-41.

Hernandez, et al., (1992), "Characterization of the Effects of Human Placental HGF on Rat Hepatocytes," *Journal of Cellular Physiology*, 150:116-121.

Higashio et al., (1990), "Identity of a Tumor Cytotoxic Factor From Human Fibroblasts and Hepatocyte Growth Factor," *Biochemical and Biophysical Research Communications*, 170(1):397-404.

Higashio et al., (1993), "Tumor cytotoxic activity of HGF-SF," *Experientia Supplementum*, 65:351-368.

Hoffman et al., (1992), "Scatter Factor is a Glycoprotein but Glycosylation is not Required for its Activity", *Biochimica et Biophysica Acta*, 1120:343-350.

Holzheimer et al., (1997), "The Challenge of Postoperative Infections: Does the Surgeon Make a Difference," *Infection Control and Hospital Epidemiology*, 18(6):449-456.

Holzheimer, (2001), "Antibiotic Induced Endotoxin Release and Clinical Sepsis: a Review," *Journal of Chemotherapy*, 13 (1):159-172.

Horton et al., (1987), "Hemodynamic Function in Acute Pancreatitis," *Surgery*, 103:538-546.

Hughes et al., (1996), "Inhibition of TNFa Improves Survival in an Experimental Model of Acute Pancreatitis," *American Surgeon*, 62:8-13.

Humes et al., (1995), "Renal Tubule Cell Repair following Acute Renal Injury," *Mineral and Electrolyte Metabolism*, 21:353-365.

Humphrey et al., (1997), "Removal of Human Immunodeficiency Virus Type 1 (HIV-1) Protease Inhibitors from Preparations of Immature HIV-1 Virions Does Not Result in an Increase in Infectivity or the Appearance of Mature Morphology," *Antimicrobial Agents and Chemotherapy*,:1017-1023.

Humphrey et al., (1996), "A Phase I Trial of HIV Protease Inhibitor KNI-272 in Patients with AIDS or Symptomatic HIV Infection," *Int. Conf. AIDS Jul. 7-12, 1996*, 11:77 (abstract no. Mo.B.1132).

Jiji Press, "Anti-AIDS Drug Tests Go to Britain," *Japan Times*, (1995).

Kageyama et al., (1993), "In Vitro Anti-Human Immunodeficiency Virus (HIV) Activities of Transition State Mimetic HIV Protease Inhibitors Containing Allophenylnorstatine," *Antimicrobial Agents and Chemotherapy*, :810-817.

Kageyama et al., (1993), "In Vitro Inhibition of Human Immunodeficiency Virus (HIV) Type 1 Replication by C2 Symmetry-Based HIV Protease Inhibitors as Single Agents or in Combinations," *Antimicrobial Agents and Chemotherapy*, 926-933.

Kaneshima et al., (1991), "Human Immunodeficiency Virus Infection of Human Lymph Nodes in the SCID-hu Mouse," *Proc. Natl. Acad. Sci.*, 88:4523-4527.

Karzai et al., (1997), "Immune Modulation and Sepsis," *Int. J. Clin. Pract.*, 51(4):232-237.

Kien et al., (1996), "Small-Volume Resuscitation Using Hypertonic Saline Improves Organ Perfusion in Burned Rats," *Anesth. Analg.*, 83:782-788.

Kinosaki et al., (1998), "Identification of heparin-binding stretches of a naturally occurring deleted variant of hepatocyte growth factor (dHGF)," *Biochimica et Biophysica Acta*, 1384(1):93-102.

Kinosaki et al., (1998), "Analysis of deleted variant of hepatocyte growth factor by alanine scanning mutagenesis: identification of residues essential for its biological function and generation of mutants with enhanced mitogenic activity on rat hepatocytes," *FEBS Letters*, 434(1-2):165-169.

Kiso, (1995), "Design and Synthesis of HIV Protease Inhibitors Containing Allophenylnorstatine As A Transition-State Mimic," *Adv. Exp. Med. Biol.*, :362:413-423.

Kondo et al., (1999), "Effects of Deletion-Type Human Hepatocyte Growth Factor on Murine Septic Model," *Journal of Surgical Research*, 85:88-95.

Lehtola et al., (1986), "Effects of Dextran 70 Versus Crystalloids in the Microcirculation of Porcine Hemorrhagic Pancreatitis," *Surgery, Gynecology & Obstetrics*, 162:556-562.

Llovera et al., (1998), "Protein Turnover in Skeletal Muscle of Tumor-Bearing Transgenic Mice Overexpressing the Soluble TNF Receptor-1," *Cancer Letters*, 130:19-27.

Llovera et al., (1998), "Role of TNF Receptor 1 in Protein Turnover During Cancer Cachexia Using Gene Knockout Mice," *Molecule and Cellular Endocrinology*, 142:183-189.

Lungarella et al., (1985), "Pulmonary Vascular Injury in Pancreatitis: Evidence for a Major Role Played by Pancreatic Elastase," *Experimental and Molecular Pathology*, 42:44-59.

Masunaga et al., 91996), "Amelioration of Disordered Hepatic Protein Synthesis by the Deleted Form of Hepatocyte Growth Factor in Models of Liver Failure in Rats," *Journal of Pharmacy and Pharmacology*, 48:876-879.

Masunaga et al., "Deleted form of hepatocyte growth factor (dHGF) increases the number of platelets in rats with liver cirrhosis," *Liver* , 17(4):192-197.

Masunaga et al., (1998), "Preventive effects of the deleted form of hepatocyte growth factor against various liver injuries," *European Journal of Pharmacology*, 342:267-279.

Mastrangelo et al., (2000), "Sepsis Decreases the Spontaneous and Agonist-Induced Contractile Activities in the Rat Portal Vein," *Journal of Hepatology*, 33:933-940.

Matsuda et al., (1995), "Hepatocyte Growth Factor Suppresses the Onset of Liver Cirrhosis and Abrogates Lethal Hepatic Dysfunction in Rats," *J. Biochem.*, 118(3):643-649.

Matsumoto et al., (1997), "HGF: its organotrophic role and therapeutic potential," *Ciba Foundation Symposium*, 212:198-214.

Matsumoto et al., (1993), "Roles of HGF as a pleiotropic factor in organ regeneration," *EXS*, 65:225-249.

Meek, (1992), "Inhibitors of HIV-1 Protease," *J. Enzyme Inhibition*, 6:65-98.

Meek et al., (1990), "Inhibition of HIV-1 Protease in Infected T-Lymphocytes by Synthetic Peptide Analogues," *Nature* , 343:90-92.

Merryman et al., (1994), "Effects of Gallium Nitrate in Nude Mice Bearing a Canine Adenocarcinoma (CAC-8) Model of Humoral Hypercalcemia of Malignancy," *J. Bone Miner. Res.*9(5):725-32.

McCune et al., (1991), "Preclinical Evaluation of Human Hematolymphoid Functions in the SCID-hu Mouse," *Immunological Reviews*, 124:45-62.

McCune et al., (1990), "Suppression of HIV Infection in AXT-Treated SCID-hu Mice," *Science*, 247:564-565.

Mimoto et al., (1991), "Rational Design and Synthesis of a Novel Class of Active Site-Targeted HIV Protease Inhibitors Containing a Hydroxymethylcarbonyl Isostere. Use of Phenylnorstatine or Allopheylnorstatine as a Transition-State Mimic," *Chem. Pharm. Bull.*,39(9):2465-2467.

Mimoto et al., (1992), "Kynostatin (KNI)-227 and -272, Highly Potent Anti-HIV Agents: Conformationally Constrained Tripeptide Inhibitors of HIV Protease Containing Allophenylnorstatine," *Chem. Pharm. Bull.*,40(8):2251-2253.

Miyazawa et al., (1989), "Molecular Cloning and Sequence Analysis of cDNA for Human Hepatocyte Growth Factor," *Biochemical and Biophysical Research Communications*, 163(2):967-973.

Moody (1982), "Changes in the serum concentrations of thyroxine-binding prealbumin and retinol-binding protein following burn injury," *Clinica Chimica Acta*, 118:87-92.

Moody et al., (1985), "The effects of septic complications upon the serum protein changes associated with thermal injury," *Ann. Clin. Biochem.*, 22:391-396.

Morimoto et al., (1991), "Hepatocyte Growth Factor Modulates Migration and Proliferation of Human Microvascular Endothelial Cells in Culture," *Biochemical and Biophysical Research Communications*, 179(2):1042-1049.

Nagoshi et al., (1998), "Hepatocyte apoptosis and hepatic expression of transforming growth factor-β mRNA during involution of hyperplastic rat liver induced by hepatocyte growth factor," *Journal of Gastroenterology and Hepatology*, 13(8):786-793.

Nishimura et al., (1997), "Serum Hepatocyte Growth Factor as a Possible Indicator of Arteriosclerosis," *Journal of Hypertension*, 15:1137-1142.

Ohlsson et al., (1991), "Pathophysiology of Acute Pancreatitis," Chapter 20 in *Pancreatic Disease, Progress and Prospects*, Johnson et al., (eds.) pp. 213-226, New York: Springer-Verlag.

Ohnishi et al., (1984), "Effects of Urinary Trypsin Inhibitor on Pancreatic Enzymes and Experimental Acute Pancreatitis," *Digestive Diseases and Sciences*, 29(1):26-32.

Penner, (1998), "Disseminated Intravascular Coagulation in Patients with Multiple Organ Failure of Non-Septic Origin," *Seminars in Thrombosis and Hemostatis*, 24(1):45-52.

Renner et al., (1985), "Death Due to Acute Pancreatitis: A Retrospective Analysis of 405 Autopsy Cases," *Digestive Diseases and Sciences*, 30(10): 1005-1018.

Roberts et al., (1990), "Rational Design of Peptide-Based HIV Proteinase Inhibitors," *Science*, 248:357-361.

Robins et al., (1993), "HIV Protease Inhibitors: Their Anti-HIV Activity and Potential Role in Treatment," *Journal of Acquired Immune Deficiency Syndromes*, 6:162-170.

Romero et al., (1991), "Nonnucleoside Reverse Transcriptase Inhibitors That Potently and Specifically Block Human Immunodeficiency Virus Type 1 Replication," *Proc. Natl. Acad. Sci.*, 88:8806-8810.

Roubenoff, (1999), "The Pathophysiology of Wasting in the Elderly," *Journal of Nutrition*, 129(1):256S-259S.

Rubin et al., (1991), "A Broad-Spectrum Human Lung Fibroblast-Derived Mitogen is a Variant of Hepatocyte Growth Factor," *Proc. Natl. Acad. Sci. USA*, 88:415-419.

Sayek et al., (1997), "Septic Complications after Biliary Tract Stone Surgery: A Review and Report of the European Prospective Study," *Hepato-Gastroenterology*, 44:959-967.

Schena, (1998), "Role of growth factors in acute renal failure," *Kidney International*, 53(Suppl. 66):S-11-S-15.

Schmaier, (2004), "Disseminated Intravascular Coagulation," accessed online at http://www.emedicine.com/MED/topic577.htm on Sep. 10, 2004.

Seki et al., (1990), "Isolation and Expression of cDNA for Different Forms of Hepatocyte Growth Factor From Human Leukocyte," *Biochemical and Biophysical Research Communications*, 172(1):321-327.

Shih, et al., (1991), "Postexposure Prophylaxis with Zidovudine Suppresses Human Immunodeficiency Virus Type 1 Infection in SCID-hu Mice in a Time-Dependent Manner," *The Journal of Infectious Diseases*, 163:625-627.

Shima et al., (1998), "Possible Involvement of p21/wafl in the Growth Inhibition of HepG2 Cells Induced by Hepatocyte Growth Factor," *Journal of Cellular Physiology*, 177(1);130-136.

Shima et al., (1994), "Hepatocyte Growth Factor and its Variant with a Delection of Five Amino Acids are Distinguishable in their Biological Activity and Tertiary Structure," *Biochemical and Biophysical Research Communications*, 200(2):808-815.

Shima et al., (1962), "Structure and biological property of fibroblast-derived tumor cytotoxic factor," *Japanese Journal of Clinical Medicine*, 50(8): 270(1962)-274(1996). (Abstract Only).

Shima et al., (1991), "Tumor Cytotoxic Factor/Hepatocyte Growth Factor from Human Fibroblasts; Cloning of its cDNA, Purification and Characterization of Recombinant Protein," *Biochemical and Biophysical Research Communications*, 180(2):1151-1158.

Shima et al., (1991), "ELISA for F-TCF (human hepatocyte growth factor/hHGF)/fibroblast-derived tumor cytotoxic factor antigen employing monoclonal antibodies and its application to patients with liver diseases," *Gastroenterologia Japonica*, 26(4):477-482.

Shima et al., (1991), "A Fibroblast-Derived Tumor Cytotoxic Factor/F-TCF (Hepatocyte Growth Factor/HGF) Has Multiple Functions in Vitro," *Cell Biology International Reports*, 15(5):397-407 (abstract only).

Shiota et al., (1992), "Hepatocyte Growth Factor Inhibits Growth of Hepatocellular Carcinoma Cells," *Proc. Natl. Acad. Sci. USA*, 89:373-377.

Sone, (1989), "Effector Mechanism of Human Monocyte-Mediated Cytotoxicity: Role of a New Tumor Cytotoxic Factor Distinct from Interleukin 1 and Tumor Necrosis Factor.alpha.," *Biotherapy*, 1:233-243.

Sone, (1985), "Kinetics and Function of Tumor Cytotoxic Factor(s) Produced by Human Blood Monocytes Activated to the Tumoricidal State," *JNCI*, 74(3):583-590.

Sone, (1986), "Potentiation of Direct Antitumor Cytotoxicity and Production of Tumor Cytolytic Factors in Human Blood Monocytes by Human Recombinant Interferon-Gamma and Muramyl Dipeptide Derivatives," *Caner Immunol. Immunother.*, 21:93-99.

Streat, 91987), "Nutritional Support in the Management of Critically Ill Patients in Surgical Intensive Care," *World J. Surg.*, 11(2):194-201.

Tahamont et al., (1982), "Increased Lung Vascular Permeability After Pancreatitis and Trypsin Infusion," *American Journal of Pathologists*, 109:15-16.

Tajima et al., (1991), "Hepatocyte Growth Factor has Potent Anti-Proliferative Activity in Various Tumor Cell Lines," *FEBS Letters*, 291(2):229-232.

Tam et al., (1992), "Intriguing Structure-Activity Relations Underlie the Potent Inhibition of HIV Protease by Norstatine-Based Peptides," *Journal of Medicinal Chemistry*, 35(7):1317-1320.

Tanaka et al., (1992), "Interleukin-1 receptor antagonist modifies the changes in vital organs induced by acute necrotizing pancreatitis in a rat experimental model," *Critical Care Medicine*, 23(5):901-908.

Tamura et al., 919930,"Enhancement of Human Hepatocyte Growth Factor Production by Interleukin-1α and 1β and Tumor Necrosis Factor-α by Fibroblasts in Culture," *J. Biol. Chem.*, 268(11):8140-8145.

Tisdale, (1997), "Biology of Cachexia," *Journal of the National Cancer Institute*, 89(32):1763-1773.

Tongdu et al., (1997), "Mechanism and Treatment of Cancer Cachexia in Tumor-Bearing Mice," *Chin. J. Oncol.*, 19(3):188-91 (Abstract only).

Tracey et al., (1988), "Cachectin/Tumor Necrosis Factor Induces Cachexia, Anemia, and Inflammation," Laboratory of Surgical Metabolism, New York Hospital-Cornell University Medical Center, New York, NY 10021; *J. Exp. Med.*, 167(3):1211-27 (Abstract Only).

Uchida et al., (1997), "HIV-1 Protease Does Not Play A Critical Role in the Early Stages of HIV-1 Infection," *Antiviral Research*, 36:107-113.

Ueda et al., (1996), "Significant Elevation of Serum Human Hepatocyte Growth Factor Levels in Patients with Acute Pancreatitis," *Pancreas*, 12(1):76-83.

Uematsu et al., (1999), "Effective Administration Route for the Deleted Form of Hepatocyte Growth Factor to Exert its Pharmacological Effects," *Journal of Pharmaceutical Sciences*, 88(1):131-135.

Weidner et al., (1991), "Evidence for the Identity of Human Scatter Factor and Human Hepatocyte Growth Factor," *Proc. Natl. Acad. Sci. USA*, 88:7001-7005.

Wichterman et al., (1980), "Sepsis and Septic Shock: A Review of Laboratory Models and a Proposal," *Journal of Surgical Research*, 29: 189-201.

Wilson et al., (1998). "Acute Pancreatitis as a model of Sepsis," *Journal of Antimicrobial Chemotherapy*, 41(Suppl. A):51-63.

Windsor et al., (1988), "Weight Loss with Physiologic Impairment: A Basic Indicator of Surgical Risk," *Ann. Surg.*, 207(3):290-296.

Xia et al., (1992), "The Effects of Burn Injury on the Acute Phase Response," *Journal of Trauma*, 32(2):245-251.

Xu et al., (1998), "Prolonged Immunodepression After Trauma and Hemorrhagic Shock," *Journal of Trauma Injury, Infection and Critical Care*, vol. 44(2), 335-341.

Yajima, et al., (1989), "Non-Septic Endotoxemia in Cirrhotic Patients," *Gastroenterologia Japonica*, 24(3):262-269.

Yamaguchi et al., (1997), "Recombinant Human Hepatocyte Growth Factor Facilitates Biliary Transport After Hepatocyte Transplantation in Eisai Hyperbilirubinemic Rats," *Digestive Diseases and Sciences*, 42(3):522-528.

Yamaguchi et al., (1991), "Effects of Site-directed Removal of N-Glycosylation Sites in Human Erythropoietin on Its Production and Biological Properties," *The Journal of Biological Chemistry*, 266(30):20434-20439.

Yamashita et al., (1998), "Effects of the Deleted Form of Hepatocyte Growth Factor on Serum Hyaluronate Levels in Rats with Liver Cirrhosis," *Journal of Veterinary Medical Science*, 60(3):359-360.

Yang et al., (1996), "Effects of Vascular Endothelial Growth Factor on Hemodynamics and Cardiac Performance," *Journal of Cardiovascular Pharmacology*, 27:838-844.

Yano et al., (1998), "Natural hepatocyte growth factor (HGF) from human serum and a bound form of recombinant HGF with Heparin sulfate are indistinguishable in their physiochemical properties," *International Journal of Biological Macromolecules*, 23(3):227-235.

Yasuda et al., (1996), "Antifibrogenic Effect of a Deletion Variant of Hepatocyte Growth Factor on Liver Fibrosis in Rats," *Hepatology*, 24(3):636-642.

Zembala et al., (1994), "The MHC Class-II and CD44 Molecules Are Involved In The Induction of Tumour Necrosis Factor (TNF) Gene Expression By Human Monocytes Stimulated With Tumour Cells," *Int. J. Cancer*, 56(2):269-74.

Zeng, et al., (1996), "Prevention of Endotoxic Shock in Rats with Hepatic Stimulating Substance," *Chinese Journal of Internal Medicine*, 35:99-102 (Abstract only).

Zhou et al., (2003), "Role of NF-κB and Cytokine in Experimental Cancer Cachexia," *World J. Gastroenterol.*, 9(7):1567-1570.

Zipp, et al., (1995), "Physical Chemical Characterization of the HIV-Protease Inhibitor Clinical Candidate," *Abstracts of the 35th ICAAC*, (1995).

Gore et al., (1999), "Review of Colloids as Fluid Resuscitation for Burn Patients," *Jpn. J. Burn Inj.*, 25(2):11-17 (abstract only).

Takehara et al., (1991), "The Structure of Hepatocyte Growth Factor (HGF) and its Physiological Activity," *Tanpakushitsu Kakusankoso*, 36(7):1227-1236 (abstract only).

Tamakuma et al., (1989), "Cancerous cachexia and Cachectin," *Strides of Medicine*, 149(5):371:373 (abstract only).

Lee, (1994), "Acute Liver Failure," *The American Journal of Medicine*, 96(Suppl 1A):3S-9S.

European Search Report for European Patent Application No. 98907158.4, dated Apr. 29, 2004, (3 Pages).

International Search Report for International Patent Application Serial No. PCT/JP98/00998, dated May 26, 1998 (2 pages).

Lake e al., (1994), "Acute Renal Failure: Directed Therapy to Enhance Renal Tubular Regeneration," *Seminars in Nephrology*, 14(1):83-87.

* cited by examiner

AGENT FOR PREVENTING AND/OR TREATING MULTIPLE ORGAN FAILURE

CROSS-REFERENCES TO RELATED APPLICATIONS

This application is a continuation of U.S. patent application Ser. No. 09/180,599 filed on Aug. 27, 1999 now abandoned, which is the U.S. National Phase Application of International Patent Application PCT/JP98/00998, filed on Mar. 11, 1998, which claims priority to Japanese Patent Application No. 74372, filed on Mar. 11, 1997, and Japanese Patent Application No. 157645, filed on May 30, 1997, the disclosures of each of the foregoing are herein incorporated by reference.

FIELD OF THE INVENTION

The present invention relates to methods for preventing and/or treating multiple organ failure.

BACKGROUND OF THE INVENTION

Onset or exacerbation of multiple organ failure can be classified into the following three categories with respect to mechanism: (1) parallel induction of several organ disorders due to the same factor, (2) induction of a specific organ dysfunction due to disorder of an organ; and (3) participation of an iatrogenic factor. Excessive insults due to severe trauma, major surgeries, infectious diseases, or shock, either directly or through various kinds of mediator, participate in the onset or deterioration of multiple organ failure by mechanism (1). In the case of multiple organ failure accompanied with organ disorder due to trauma or primary hepatic insufficiency, participation of mechanism (2) through organ correlation mechanism will largely contribute to the onset or deterioration thereof. By mechanism (3), medical care carried out during intensive care or care to correspond with an organ disorder may result in the other organ disorder. In patients, these three mechanisms participate to the development or deterioration of multiple organ failure in a complex manner. The prognosis of patients of multiple organ failure is generally very poor and, in fact, the survival rate is low as 20–30% in spite of a wide variety of corresponding treatments.

BRIEF SUMMARY OF THE INVENTION

The present inventors searched for an agent for preventing and/or treating multiple organ failure and found that multiple organ failure caused by burn, disseminated intravascular coagulation (DIC), circulatory failure, hemorrhagic shock, infectious disease, acute pancreatitis, ischemic disorder, hepatorenal syndrome, gastrointestinal hemorrhage, nutritional metabolic failure, terminal cancer, acquired immunodeficiency syndrome (AIDS), deterioration of systemic conditions due to radiation affection and cachexia can be prevented or treated with tumor cytotoxic factor-II (TCF-II) which is a glycoprotein derived from human fibroblast or hepatocyte growth factor (HGF) which is a proteineous substance derived from blood of a patient with fulminating hepatitis. Accordingly, an object of the present invention is to provide an agent for preventing and/or treating multiple organ failure comprising TCF-II or HGF as an effective ingredient.

BRIEF DESCRIPTION OF THE DRAWINGS

In FIGS. 1–10, ○ represents the TCF-II or HGF treatment group and ● represents the vehicle treatment group.

DETAILED DESCRIPTION OF THE INVENTION

Figure 1:
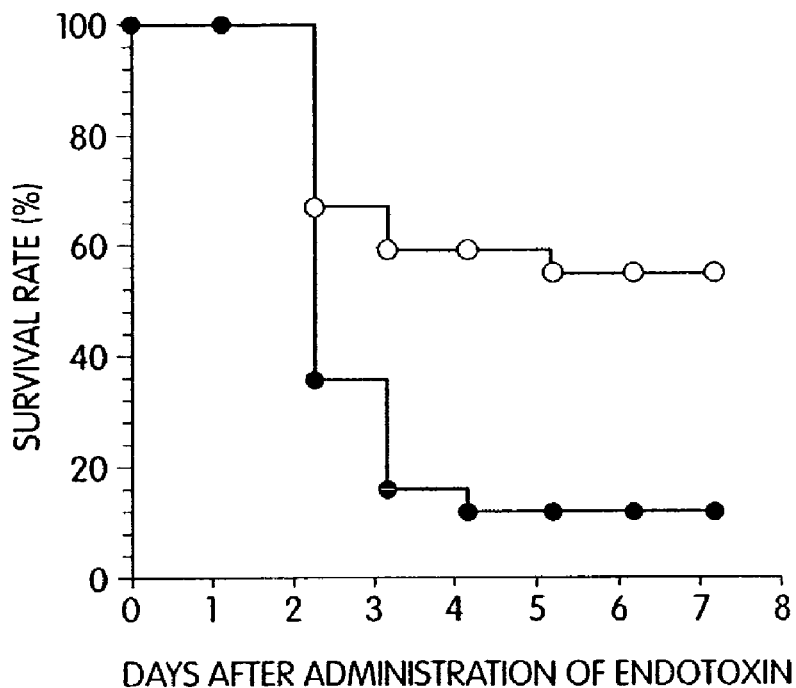
FIG. 1 shows the protective effect of TCF-II on endotoxin-induced multiple organ failure described in Example 4.

The agent of the present invention for preventing and/or treating multiple organ failure can be useful for preventing and/or treating the development from burn, disseminated intravascular coagulation (DIC), circulatory failure, hemorrhagic shock, infectious disease, acute pancreatitis, ischemic disorder, hepatorenal syndrome, gastrointestinal hemorrhage, nutritional metabolic failure, terminal cancer, acquired immunodeficiency syndrome (AIDS), deterioration of systemic conditions due to radiation affection and cachexia etc. These kinds of multiple organ failure may result from burn, surgical operation, administration of chemical substances (including medicine), radiation, or other disorder.

TCF-II, which is an effective ingredient of the present invention, is a glycoprotein derived from human fibroblast having the following characteristics:

1) Molecular weight (by SDS electrophoresis)

under non-reducing conditions: 78,000 ± 2,000 or 74,000
   under reducing conditions: 52,000 ± 2,000 (common b and A)
   30,000 ± 2,000 (b and B)
   26,000 ± 2,000 (b and C)

2) Isoelectric point: 7.4–8.6

TCF-II can be obtained by adsorbing culture medium of human fibroblast on an ion exchange column then purifying the elute by affinity chromatography (as described in WO 90/10651) or by genetic engineering manipulation (as described in WO 92/01053). TCF-II which is an effective ingredient of the present invention can be derived from fibroblast or produced by genetic engineering manipulation using microbial cells or other cells based on the genetic sequence described in patent application WO 90/10651. Further, TCF-II obtained by genetic engineering manipulation described in WO 92/01053 can be also used.

TCF-II with different carbohydrate chain or without carbohydrate chain due to difference of host cell or microbial organism can be also used. However, since carbohydrate chain correlate to metabolic rate in a biological body, a TCF-II protein with carbohydrate chain can be preferably used.

TCF-II obtained by the methods described above can be concentrated and purified by isolation and purification methods known in the art. For example, TCF-II may be purified by precipitation with organic solvent, salting-out, gel permeation, affinity chromatography using monoclonal antibody, or electrophoresis. Purification by affinity chromatography using monoclonal antibody can be carried out using monoclonal antibody described in Japanese unexamined laid open patent application No. 97(1993). TCF-II thus obtained can be lyophilized or frozen.

Substances having the same activity as TCF-II can be used as the agent of the present invention. For example, hepatocyte growth factor (HGF) (described in Japanese unexamined laid open patent application No. 22526 (1988)) can be used as the agent of the present invention. HGF is formed by insertion of 5 amino acids into TCF-II protein or Scattered Factor (SF); Gherardi and Stocker, Nature, 346, 228 (1990).

HGF, which is an effective ingredient has an activity of inducing proliferation of hepatic cells, was isolated from the blood of a patient with fulminating hepatitis and is a known protein with the following characteristics (as described in Japanese Patent No. 2564486):

1) Molecular weight (SDS-PAGE); under non-reducing conditions is 76,000–92,000;

2) The ability of HGF to induce hepatic cell proliferation was not deactivated by heating the HGF protein at 56° C. for 15 minutes, but heating the HGF protein at 80° C. for 10 minutes did deactivated the ability of HGF to induce hepatic cell proliferation;

3) Digestion with trypsin or chymotrypsin deactivated the ability of HGF to induce hepatic cell proliferation; and 4) HGF demonstrates an affinity with heparin.

HGF can be obtained by heating plasma at 56° C. for about 15 minutes, taking precipitated fraction at the ammonium sulfate concentration of 1.1–1.2 M, followed by purification using gel permeation and ion exchange chromatography such as DEAE anion exchange chromatography. Alternatively, HGF can be obtained by genetic engineering manipulation using HGF cDNA (BRRC 163, 967–973, 1989, or Japanese unexamined laid open Patent Application No. 97 (1993)).

The agent of the present invention for preventing and/or treating multiple organ failure can be administered intravenously, intramuscularly or subcutaneously. These pharmaceutical preparations can be prepared according to a known pharmaceutical preparation methods and, if necessary, pH conditioner, buffer and/or stabilizer can be added thereto. Dosage of the present agent can be different depending on the severity of symptom, health conditions, age, body weight of a patient. Though the dose will not be restricted, pharmaceutical preparation comprising 0.6 mg-600 mg-TCF-11/day is preferred, and pharmaceutical preparations comprising 6 mg-60 mg-TCF-II/day are most preferred. The preparation can be administered to an adult person in a single dose or in multiple doses. The dose of HGF can be nearly the same as that of TCF-II.

Administration as described above can prevent multiple organ failure caused by various kinds of mechanism described before or alleviate symptom thereof.

EXAMPLES

The present invention will be described below in detail by the following examples. However, these are only examples and the present invention will not limited thereby.

Example 1

Purification of TCF-II

According to a method described in WO 90/10651 and the method of Higashio et. al. (Higashio, K et. al, B.B.R.C., Vol. 170, pp 397–404 (1990)), human fibroblast cells were cultured to obtain purified TCF-II. $3 \times 10^6$ human fibroblast IMR-90 (ATCC CCL 186) cells were placed in a roller bottle containing 100 ml DMEM medium including 5% calf fetal serum and cultured by rotating it at the rate of 0.5–2 rpm for 7 days. When the total number of cells reached $1 \times 10^7$ the cells were detached from the walls of the roller bottle by trypsin digestion and collected at the bottom of bottle. 100 g of ceramic with the size of 5–9 mesh (Toshiba Ceramic) was sterilized and place in the roller bottle, Culture was continued for 24 hours. After then, 500 ml of the above culture medium was added to the roller bottle and the culture was again continued. The total volume of culture medium was recovered every 7–10 days and fresh medium was supplemented. Production continued in this manner for 2 months and 4 liters of culture medium was recovered per roller bottle. The specific activity of TCF-II in culture medium obtained by the method described above was 32 µg/ml. Culture medium (750 L) was concentrated by ultrafiltration using membrane filter (MW 6,000 cut; Amicon) and purified by 4-step chromatography, that is, CM-Sephadex C-50 (Pharmacia), Con-A Sepharose (Pharmacia), Mono S column (Pharmacia), Heparin-Sepharose (Pharmacia) to yield purified TCF-II. This TCF-II had the same weight and isoelectric, point as described above.

Example 2

Production of Recombinant TCF-II

According to the method described in WO 92/01053, cells transformed with TCF-II gene were cultured and purified TCF-II was obtained. That is, transformed Namalwa cell was cultured and 20 L of culture medium was obtained. This culture medium was treated by CM-Sephadex C-50 chromatography, Con-A Sepharose CL-6B chromatography, and finally HPLC equipped with a Mono S column to yield about 11 mg of recombinant TCF-II. This TCF-II had the same molecular weight and isoelectric, point as described above.

Example 3

Production of Recombinant HGF

Expression vector of HGF cDNA was constructed by inserting 2.4 kb fragment of transcription unit of mouse dihydrofolate reductase (DBFR) into Nhe I site of plasmid pcDNA1 and, further, inserting 2.3 kb of HGF cDNA cloned by Miyazawa (BBRC 163, 967–973, 1999) into the downstream of cytomegalovirus (CMV) promoter. The constructed HGF cDNA expression vector (µg and pSV2 neo 1 µg) were co-transfected into Namalwa cell by liposome intervened transfection method using LIPOFECTIN® (N-

[1-(2,3-dioleyloxy)propyl]-n,n,n-trimethlammonium chloride (DOTMA) and dioleoyl phosphotidylethanolamine (DOPE)), Life Technologies, Inc., Gaithersburg, Md. After transformed cells were screened by G418 resistance, gene amplification was carried out using methotrexate (MTX). HGF highly producing cell line was cultured in 2 L roller bottles containing 1 L DMEM medium including 5% bovine serum for 7 days. Culture was carried out using 20 roller bottles (2 rpm) and 21 L of culture medium was obtained. The culture medium obtained contained 4 mg/L HGF.

According to a modified method of Higashio (Higashio et. al., vol. 170, 397–404, 1990), 20 L of culture medium containing HGF was purified by 3 step chromatography, that is, CM-Sephadex C-50 (Pharmacia), Mono S column (Pharmacia) and Heparin 5-PW (Toso) and purified HGF with homogeneous mobility of SDS-electrophoresis was obtained in about 60% yield.

Example 4

Protective Effect of TCF-II on Endotoxin-Induced Multiple Organ Failure

TCF-II (100 μg/mouse) obtained in Example 2 was administered intravenously to 7 week old male ICR mice (25 mice/group) twice daily for 5 days (only at the final day, once a day). The control group was treated with the vehicle, citric acid buffer solution with pH 6.03, hereinafter the same solution was used as control group). At 6 hours after the final administration, lethal dose of endotoxin (E coli lipopolysaccharide (LPS); 20 mg/kg, Difco Laboratories, Detroit, Mich.) was administered intravenously. The survival rates thereof was shown in FIG. 1. The survival rates on day 4 or later was 12% (3/25 mice) in the vehicle group, and those in the TCF-II group were 56% (14/25 mice).

From these results, TCF-II was confirmed to show an excellent protective effect on endotoxin-induced multiple organ failure.

Example 5

Protective Effect of HGF on Endotoxin-Induced Multiple Organ Failure

Figure 2:
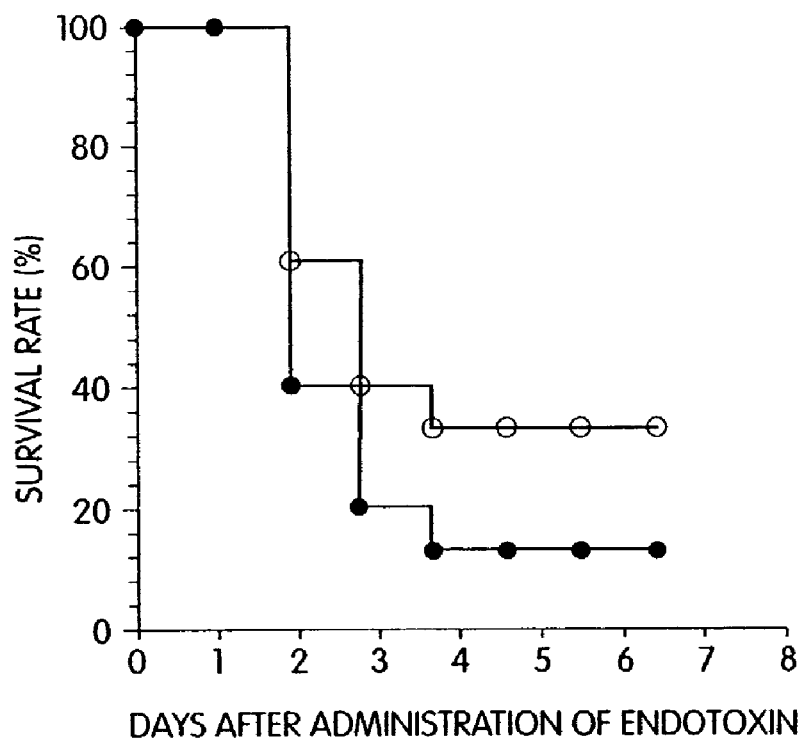
FIG. 2 shows the protective effect of HGF on endotoxin-induced multiple organ failure described in Example 5.

HGF (100 μg/mouse) obtained in by the method described in Example 3 was administered intravenously to 7 weekold male ICR mice (15 mice/group) twice daily for 5 days (only at the final day, once a day). The control group was treated with the vehicle (citric acid buffer solution with pH 6.03). At 6 hours after the final administration, lethal dose of endotoxin (E coli lipopolysaccharide (LPS); 20 mg/kg, Difco Laboratories, Detroit, Mich.) was administered intravenously. The survival rates for the two groups is shown in FIG. 2. The survival rate on day 4 or later for the vehicle group was 13% (2/15 mice), and the survival rate for the group treated with 1 mg/kg of HGF treated group was 33% (5/15 mice). From these results, HGF was confirmed to show an excellent protective effect on endotoxin-induced multiple organ failure.

Example 6

Protective Effect of TCF-II on Endotoxin-Induced Multiple Organ Failure

Animal model of multiple organ failure was made by continuously injecting endotoxin (E coli lipopolysaccharide (LPS); 10 mg.kg/day, Difco Laboratories, Detroit, Mich.) to 6 week old male Wister rats using osmotic pump (Model 7 I2001, Alzet). After then, animals were divided into two groups (9 rats/group) and Vehicle or TCF-II (1 mg/kg) was administered intravenously once a day for 7 days. The results of clinical examination at the day after the final administration are shown in Table 1. In the vehicle group, the serum levels of total protein, albumin, total cholesterol and the plasma levels of plasminogen were decreased the day after the final administration, indicating that these rats were developing cachexia, but those in TCF-II treated group were significantly improved (Table 1). From these results, TCF-II was confirmed to show an excellent protective effect on multiple organ failure caused by endotoxin-induced cachexia.

TABLE 1

| | | LPS-induced model | |
|---|---|---|---|
| Assay | Normal | Vehicle | TCF |
| Total protein(g/dl) | 5.4 ± 0.1 | 4.5 ± 0.1 | 5.5 ± 0.1** |
| Albumin(g/dl) | 2.5 ± 0.1 | 1.8 ± 0.1 | 2.4 ± 0.0** |
| Plasminogen(%) | 105.5 ± 7.1 | 74.4 ± 3.6 | 96.6 ± 2.7** |
| Total cholesterol(mg/dl) | 73.2 ± 2.3 | 59.0 ± 3.6 | 88.6 ± 2.9** |

(**significant difference ($p < 0.01$) from vehicle administered group)

Example 7

Figure 3:
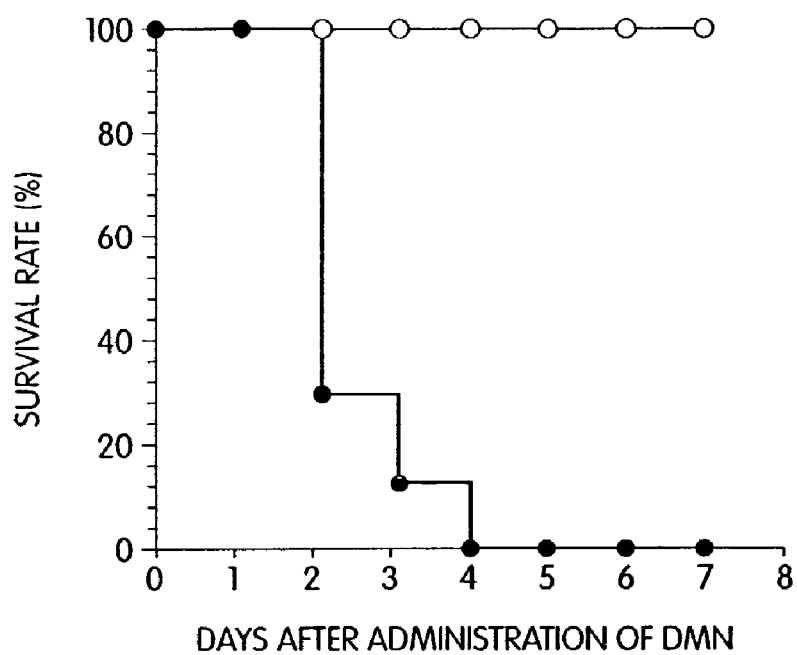
FIG. 3 shows the protective effect of TCF-II on dimethyinitrosamine-induced multiple organ failure described in Example 7.

Protective Effect of TCF-II on Dimethylnitrosamine-Induced Multiple Organ Failure TCF-II (100 μg/mouse) was administered intravenously to 7 weeks old male ICR mice (25 mice/group) twice daily for 5 days (only at the final day, once a day). The control group was treated with the vehicle. At 6 hours after the final administration, a lethal dose of 0.15% dimethynitrosoamine (DMN) (vehicle: physiological saline solution, 0.1 ml/10 g body weight, Tokyo-kasei-kogyo) was administered intravenously. The results of clinical examination of mice at 24 hours after the onset is shown in Table 2 and the survival rates of both groups of mice are shown in FIG. 3. In the vehicle group, the plasma levels of glutamic oxaloacetic transaminase (GOT) and glutamic-pyruvic transaminase (GPT) at 24 hours after DMN administration were remarkably increased and the plasma clotting time was prolonged, but those of TCF-II treated group were significantly suppressed (Table 2). Further, in the vehicle group, all the mice died after 4 days, and all the mice in the TCF-II group survived (FIG. 3). From these results, TCF-II was confirmed to show an excellent protective effect on dimethylnitrosamine-induced multiple organ failure.

TABLE 2

| | | DMN-induced model | |
|---|---|---|---|
| Assay | Normal | Vehicle | TCF-II |
| GOT(U/L) | 42 ± 2 | 810 ± 252 | 51 ± 8** |
| GPT(U/L) | 28 ± 3 | 1580 ± 506 | 97 ± 21** |
| Plasma clotting time(sec) | 17 ± 0.0 | 22 ± 2.2 | 17 ± 0.1** |

(**significant difference ($p < 0.01$) from vehicle group)

Example 8

Figure 4:
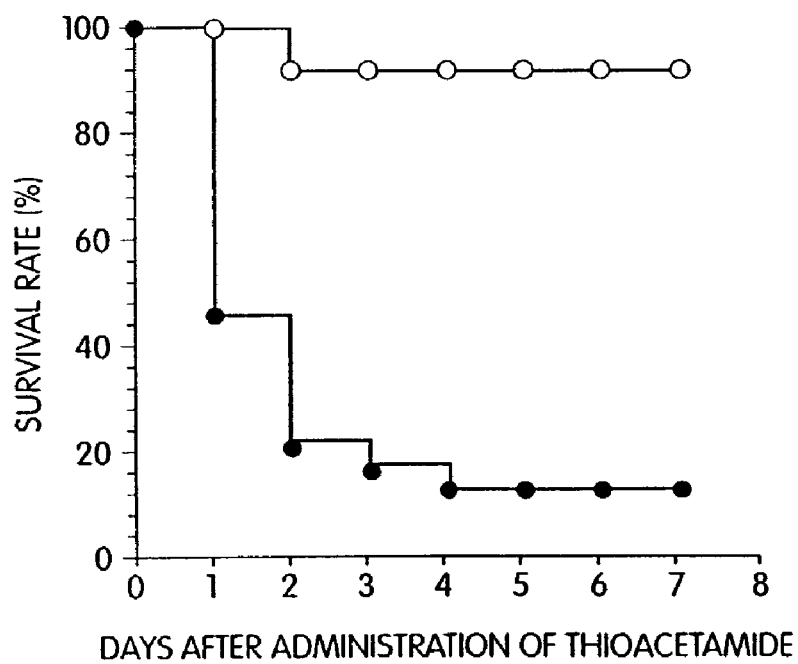
FIG. 4 shows the protective effect of TCF-II on thioacetamide intoxication-induced multiple organ failure described in Example 8.
Figure 5:
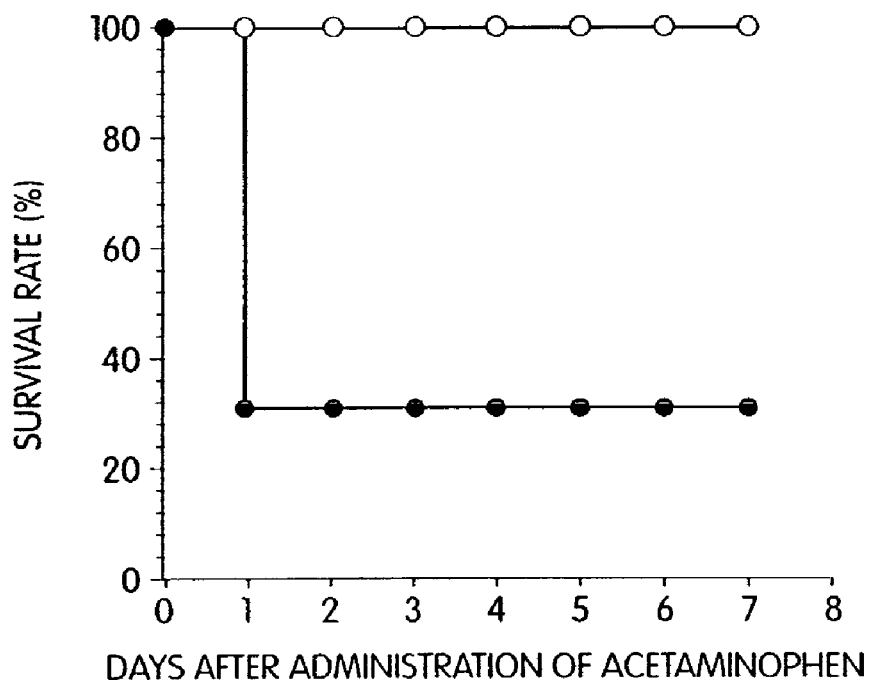
FIG. 5 shows the protective effect of TCF-II on acetaminophen intoxication-induced multiple organ failure described in Example 8.

Protective effect of TCF-II on Drug Intoxication-Induced Multiple Organ Failure TCF-II (100 μg/mouse) was administered intravenously to 7 week old male ICR mice (25 mice/group) twice daily for 5 days (only at the final day, once a day). The control group was treated with the vehicle. At 6 hours after the final administration, a lethal dose of thioacetamide (600 mg/kg Wako-junyaku) or acetaminophen (800 mg/kg, Sigma) was administered. The survival rates for both groups are shown in FIG. 4 and FIG. 5. In the thioacetamide experiment, the survival rate after day 4 or later of vehicle administered group was 12% (3/25 mice), and the survival rate of the TCF-II administered group was 93% (23/25 mice). In the acetaminophen experiment, 68% (17/25 mice) of vehicle administered group died at the day after acetaminophen treatment, and all of the mice of TCF-II administered group survived. From these results, TCF-II was confirmed to show an excellent protective effect on drug intoxication-induced multiple organ failure.

Example 9

Figure 6:
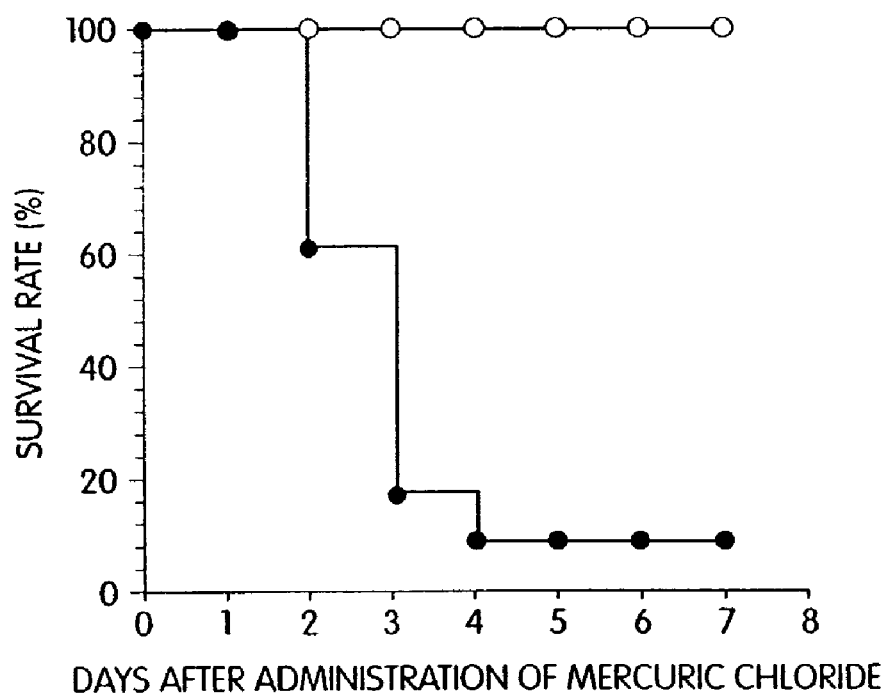
FIG. 6 shows the protective effect of TCF-II on multiple organ failure caused by mercuric chloride-induced renal insufficiency described in Example 9.

Protective Effect of TCF-II on Multiple Organ Failure Caused by Mercuric Chloride-Induced Renal Insufficiency TCF-II (1 μg/mouse) was administered intravenously to 7 week old male ICR mice (25 mice/group) twice daily for 5 days (only at the final day, once a day). The control group was treated with the vehicle. At 6 hours after, the final administration, lethal dose of mercuric chloride (Wako-junyaku) was administered intravenously. The survival rates of both groups are shown in FIG. 6. Though the survival rate after 4 days of vehicle administered group was 8% (2/25 mice), all of the mice of TCF-II administered group survived.

From these results, TCF-II was confirmed to show an excellent protective effect on multiple organ failure caused by mercuric chloride-induced.

Example 10

Protective Effect on Trypsin-Induced Multiple Organ Failure

Figure 7:
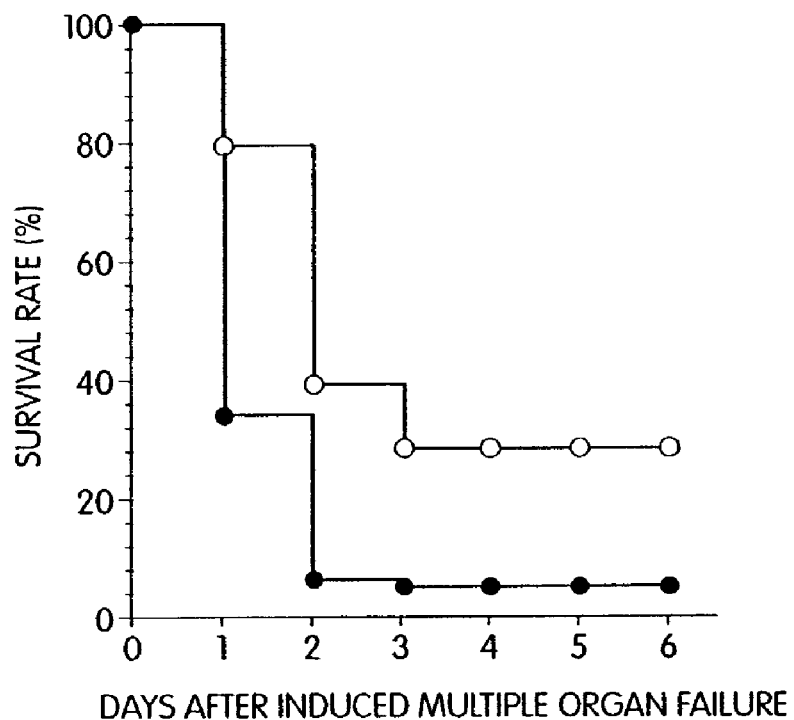
FIG. 7 shows the protective effect of TCF-II on trypsin-induced multiple organ failure described in Example 10.

Vehicle (55 rats/group) or 1 mg/kg TCF-II (35 rats/group) was administered intravenously to 8 week old male Wister rats twice daily for 5 days (10 times). At the day after the final administration, 0.16 ml of mixed solution of lethal dose of trypsin (Sigma; 50000 U/ml) and taurocolic acid (Sanko-junyaku; 100 mg/ml) was injected into pancreas through the common bile duct. The survival rates for both groups are shown in FIG. 7. Though the survival rate after 6 days of vehicle administered group was 5% (3/55 rats), the survival rate of the TCF-II treated group was 29% (10/35 rats). From these results, TCF-II was confirmed to show an excellent protective effect on trypsin-induced multiple organ failure.

Example 11

Protective Effect TCF-II on Burn-Induced Multiple Organ Failure

Figure 8:
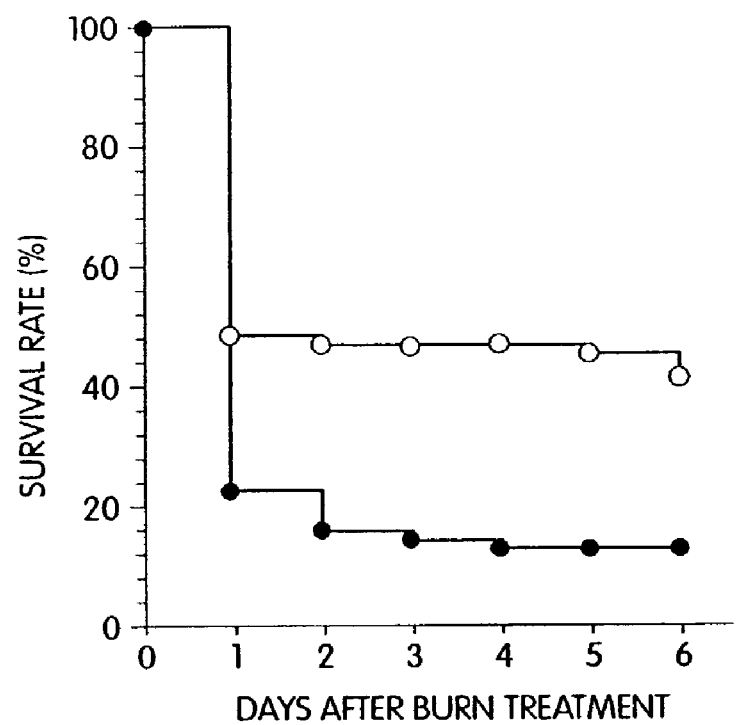
FIG. 8 shows the protective effect of TCF-II on burn-induced multiple organ failure described in Example 11.

Vehicle or 1 mg/kg TCF-II was administered intravenously to 7 week old male Wister rats (50 rats/group) twice daily for 6 days (only once a day on the final day). At 6 hours after the final administration, 25% burn (250° C., 30 sec.) was made on shaved back with a heating plate (Iwaki-glass). The survival rates of both groups are shown in FIG. 8, and the results of clinical examination performed 4 hours after burn treatment is shown in Table 3. Decrease of circulating volume of Plasma (increase in Ht value, decrease in total protein, decrease in albumin) and hepatic derangement were observed and onset of multiple organ failure caused by burn shock was confirmed (Table 3). In addition, though the survival rates after 6 days of vehicle administered group was 12% (6/50 rats), the survival rate of TCF-II administered group was 40% (20/55 rats) (FIG. 8). From these results, TCF-II was confirmed to show an excellent protective effect on burn-induced multiple organ failure.

TABLE 3

|  | Before burn treatment | 4 hours after burn treatment |
|---|---|---|
| Hematocrit value (%) | 44.8 ± 1.8 | 53.9 ± 3.6 |
| Total protein (g/d) | 7.2 ± 0.5 | 5.8 ± 0.7 |
| Albumin (g/dl) | 3.1 ± 0.2 | 2.4 ± 0.3 |
| GPT (U/L) | 20.5 ± 5.8 | 150.0 ± 30.4 |
| Urea nitrogen (mg/dl) | 21.5 ± 1.9 | 43.5 ± 7.3 |

Example 12

Protective Effect on Burn-Induced Multiple Organ Failure

Figure 9:
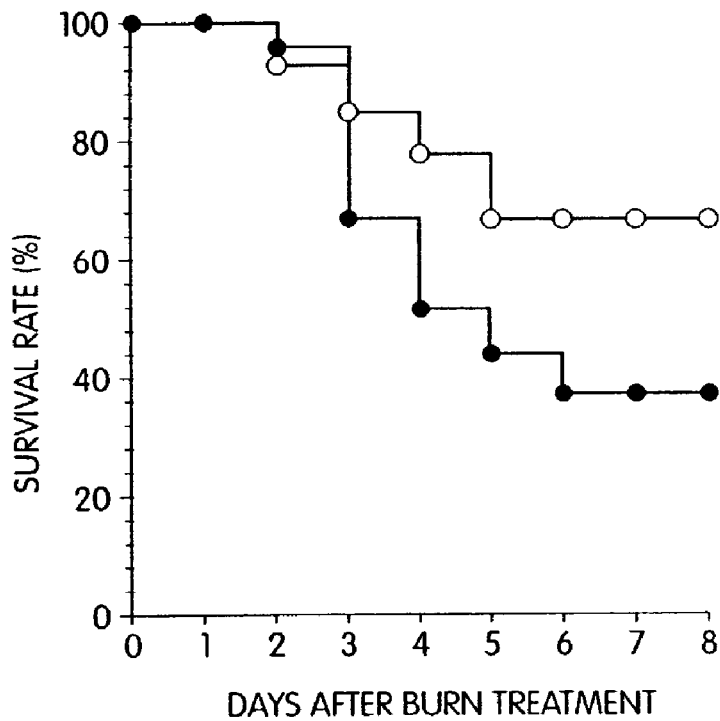
FIG. 9 shows the protective effect of TCF-II on burn-induced multiple organ failure described in Example 12.

In 9 week old male Wister rats, 40% burn was made using 85° C. hot water. After burn, rats were divided into 2 groups consisting of 27 rats each. Vehicle or 1 mg/kg TCF-II was administered intravenously 3 times/daily for 3 days (9 times). The survival rates of both groups are shown in FIG. 9. Though the survival rate after 8 days of vehicle administered group was 37% (10/27 rats), the survival rate of TCF-II administered group was 67% (18/27 rats). From these results, TCF-II was confirmed to show an excellent protective effect on burn-induced multiple organ failure.

Example 13

Protective Effect of HGF on Burn-Induced Multiple Organ Failure

Figure 10:
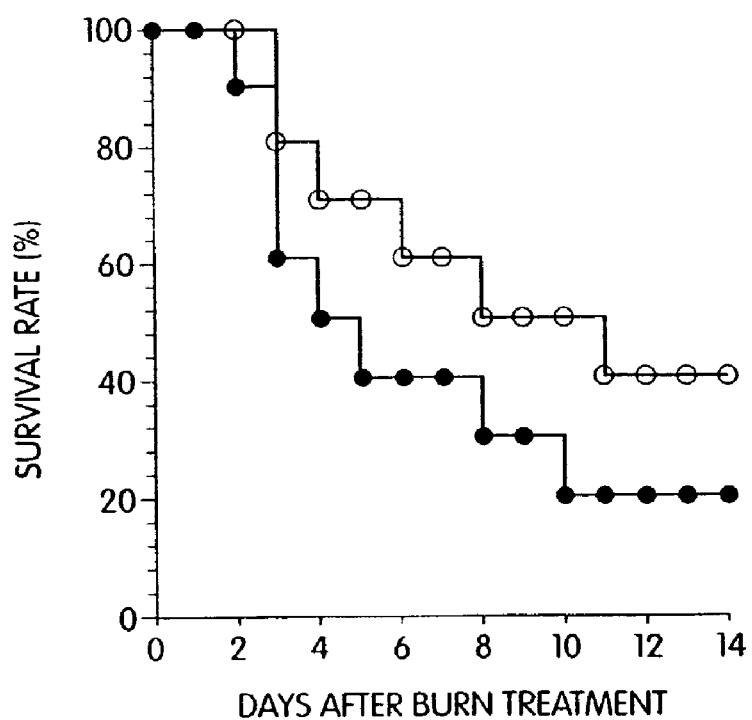
FIG. 10 shows the protective effect of HGF on burn-induced multiple organ failure described in Example 13.

In 9 week old male Wister rats, 40% burn was made using 85° C. hot water. After burn, rats were divided into 2 groups consisting of 10 rats each. Vehicle or 1 mg/kg HGF was administered intravenously 3 times/daily for 3 days (9 times). The survival rates for both groups are shown in FIG. 10. Though the survival rates after 11 days of vehicle administered group was 20% (2/10 rats), the survival rate of HGF administered group was 40% (4/10 rats). From these results, HGF was confirmed to show an excellent protective effect on burn-induced multiple organ failure.

Example 14

Manufacture of pharmaceutical preparation of TCF-II

An example of manufacturing injections of recombinant TCF-II obtained by the method described in Example 2 was shown.

| (1) | TCF-II | 20 μg |
| | human serum albumin | 100 mg |

The above composition was dissolved in citric acid buffer solution with pH 6.03 (consisting of 10 mM sodium citrate, 0.3 M sodium chloride, 0.03% polysolbate) so that the total volume would be 20 ml. The solution was then divided into vials containing 2 ml each after sterilization and sealed after lyophilization.

| (2) | TCF-II | 40 μg |
| | Tween 80 | 1 mg |
| | human serum albumin | 100 mg |

The above composition was dissolved in physiological saline solution for injections so that the total volume would be 20 ml. The solution was then divided into vials containing 2 ml each after sterilization and sealed after lyophilization.

| (3) | TCF-II | 20 μg |
| | Tween 80 | 2 mg |
| | Sorbitol | 4 g |

The above composition was dissolved in citric acid buffer solution with pH 6.03 so that the total volume would be 20 ml. The solution was then was divided into vials containing 2 ml each after sterilization and sealed after lyophilization.

| (4) | TCF-II | 40 μg |
| | Tween 80 | 1 mg |
| | Glycine | 2 g |

The above composition was dissolved in physiological saline solution for injections so that the total volume would be 20 ml. The solution was then was divided into vials containing 2 ml each after sterilization and sealed after lyophilization.

| (5) | TCF-II | 40 μg |
| | Tween 80 | 1 mg |
| | Solbitol | 2 g |
| | Glycine | 1 g |

The above composition was dissolved in physiological saline solution for injections so that the total volume would be 20 ml. The solution was then was divided into vials containing 2 ml each after sterilization and seated after lyophilization.

| (6) | TCF-II | 20 μg |
| | Sorbitol | 4 g |
| | human serum albumin | 50 mg |

The above composition was dissolved in citric acid buffer solution with pH 6.03 so that the total volume would be 20 ml. The solution was then divided into vials containing 2 ml each after sterilization and sealed after lyophilization.

| (7) | TCF-II | 40 μg |
| | Glycine | 2 g |
| | human serum albumin | 50 mg |

The above composition was dissolved in physiological saline solution for injections so that the total volume would be 20 ml. The solution was then divided into vials containing 2 ml each after sterilization and sealed after lyophilization.

| (8) | TCF-II | 40 μg |
| | human serum albumin | 50 mg |

The above composition was dissolved in citric acid buffer solution with pH 6.03 so that the total volume would be 20 ml. The solution was then divided into vials containing 2 ml each after sterilization arid sealed after lyophilization.

Example 15

Manufacture of Pharmaceutical Preparation of HGF

An example of manufacturing injections of recombinant HGF obtained by the method described in Example 3 was shown.

| (1) | HGF | 40 μg |
| | human serum albumin | 100 mg |

The above composition was dissolved in citric acid buffer solution with pH 6.03 so that the total volume would be 20 ml. The solution was then divided into vials containing 2 ml each after sterilization and sealed after lyophilization.

| (2) | HGF | 20 μg |
| | Tween 80 | 1 mg |
| | human serum albumin | 100 mg |

The above composition was dissolved in physiological saline solution for injections so that the total volume would be 20 ml. The solution was then divided into vials containing 2 ml each after sterilization and sealed after lyophilization.

| (3) | HGF | 30 μg |
| | Sorbitol | 4 g |
| | human serum albumin | 50 mg |

The above composition was dissolved in 0.01 M phosphate buffer solution with pH 7.0 so that the total volume would be 20 ml. The solution was then divided into vials containing 2 ml each after sterilization and sealed after lyophilization.

An agent is provided for preventing and/or treating multiple organ failure comprising TCF-II or HGF as an effective ingredient is provided by the present invention. The agent for preventing and/or treating multiple organ failure of the present invention will be useful for preventing and/or treating the development from burn, disseminated intravascular coagulation (DIC), circulatory failure, hemorrhagic shock, infectious disease, acute pancreatitis, ischemic disorder, hepatorenal syndrome, gastrointestinal hemorrhage, nutritional metabolic failure, terminal cancer, acquired immunodeficiency syndrome (AIDS), deterioration of systemic conditions due to radiation affection and cachexia to multiple organ failure.

The invention claimed is:

1. A method for improving the survival rate of a patient exposed to an endotoxin, the method comprising the step of administering tumor cytotoxic factor-II (TCF-II) intravenously, intramuscularly or subcutaneously to said patient in an amount effective to improve the survival rate of said patient, wherein the TCF-II is administered before or after said patient is exposed to an endotoxin.

2. A method for improving the survival rate of a patient exposed to an endotoxin, the method comprising the step of administering hepatocyte growth factor (HGF) intravenously, intramuscularly or subcutaneously to said patient in an amount effective to improve the survival rate of said patient, wherein the HGF is administered before or after said patient is exposed to an endotoxin.

3. A method for improving the survival rate of a patient exposed to a substance in an amount associated with the induction of multiple organ failure, the method comprising the step of administering tumor cytotoxic factor-II (TCF-II) intravenously, intramuscularly or subcutaneously to said patient in an amount effective to improve the survival rate of said patient, wherein the TCF-II is administered before or after the patient is exposed to the substance.

4. A method for improving the survival rate of a patient exposed to a substance in an amount associated with the induction of multiple organ failure, the method comprising the step of administering hepatocyte growth factor (HGF) intravenously, intramuscularly or subcutaneously to said patient in an amount effective to improve the survival rate of said patient, wherein the HGF is administered before or after said patient is exposed to the substance.

* * * * *